United States Patent
Lipowicz

(10) Patent No.: US 10,321,712 B2
(45) Date of Patent: Jun. 18, 2019

(54) ELECTRONIC VAPING DEVICE

(71) Applicant: Altria Client Services LLC, Richmond, VA (US)

(72) Inventor: Peter Lipowicz, Midlothian, VA (US)

(73) Assignee: Altria Client Services LLC, Richmond, VA (US)

( * ) Notice: Subject to any disclaimer, the term of this patent is extended or adjusted under 35 U.S.C. 154(b) by 469 days.

(21) Appl. No.: 15/083,507

(22) Filed: Mar. 29, 2016

(65) Prior Publication Data

US 2017/0280768 A1    Oct. 5, 2017

(51) Int. Cl.
| | | |
|---|---|---|
| A24F 47/00 | (2006.01) |
| A61M 11/04 | (2006.01) |
| A24F 1/32 | (2006.01) |
| A61M 15/06 | (2006.01) |
| A61M 16/00 | (2006.01) |

(52) U.S. Cl.
CPC .............. *A24F 47/008* (2013.01); *A24F 1/32* (2013.01); *A61M 11/042* (2014.02); *A61M 15/06* (2013.01); *A61M 2016/0021* (2013.01); *A61M 2205/0244* (2013.01); *A61M 2205/3653* (2013.01); *A61M 2205/8206* (2013.01)

(58) Field of Classification Search
CPC ................ A61M 11/042; A61M 15/06; A61M 2016/0021; A61M 2205/0244; A61M 2205/3653; A61M 2205/8206; A24F 47/008; A24F 1/32
USPC ........................................................ 392/395
See application file for complete search history.

(56) References Cited

U.S. PATENT DOCUMENTS

| | | | |
|---|---|---|---|
| 4,946,931 A | 8/1990 | Gori | |
| 4,993,436 A | 2/1991 | Bloom, Jr. | |
| 5,894,841 A | 4/1999 | Voges | |
| 6,155,268 A * | 12/2000 | Takeuchi | A24F 47/008 |
| | | | 131/194 |
| 7,743,766 B2 | 6/2010 | Gupta et al. | |
| 8,511,318 B2 | 8/2013 | Hon | |
| 2010/0031968 A1 | 2/2010 | Sheikh et al. | |
| 2012/0090630 A1* | 4/2012 | Hon | A24F 47/002 |
| | | | 131/273 |

(Continued)

FOREIGN PATENT DOCUMENTS

| | | |
|---|---|---|
| EP | 2319334 A1 | 5/2011 |
| GB | 2494315 A | 3/2013 |

(Continued)

OTHER PUBLICATIONS

International Search Report and Written Opinion for corresponding International application No. PCT/EP2017/057453 dated Jun. 7, 2017.

*Primary Examiner* — Brian W Jennison
(74) *Attorney, Agent, or Firm* — Harness, Dickey & Pierce, P.L.C.

(57) ABSTRACT

A reservoir assembly for an electronic vaping device includes a reservoir configured to store a pre-vapor formulation, a tube including a first end and a second end, and a sleeve at least partially surrounding the second end of the tube. The first end of the tube extends into the reservoir. The second end of the tube protrudes from the reservoir. The tube includes a hole in a sidewall of the tube at the second end. The sleeve is formed of a wicking material. The sleeve is in fluid communication with the hole in the sidewall of the tube.

20 Claims, 1 Drawing Sheet

(56) References Cited

U.S. PATENT DOCUMENTS

| | | |
|---|---|---|
| 2013/0160765 A1 | 6/2013 | Liu |
| 2013/0192623 A1 | 8/2013 | Tucker et al. |
| 2013/0306065 A1 | 11/2013 | Thorens et al. |
| 2014/0069424 A1 | 3/2014 | Poston et al. |
| 2014/0346689 A1* | 11/2014 | Dubief .................. A24F 47/008 261/142 |
| 2015/0020823 A1 | 1/2015 | Lipowicz et al. |
| 2015/0083147 A1 | 3/2015 | Schiff et al. |
| 2015/0264979 A1 | 9/2015 | Thorens et al. |
| 2015/0313275 A1 | 11/2015 | Anderson et al. |

FOREIGN PATENT DOCUMENTS

| | | |
|---|---|---|
| JP | 2008104966 A | 5/2008 |
| WO | WO-2011/042212 A1 | 4/2011 |
| WO | WO-2013/083634 A1 | 6/2013 |
| WO | WO-2015/011703 A1 | 1/2015 |
| WO | WO-2015/139188 A1 | 9/2015 |
| WO | WO-2016/014652 A1 | 1/2016 |

\* cited by examiner

ELECTRONIC VAPING DEVICE

BACKGROUND

Field

The present disclosure relates to an electronic vaping or e-vaping device configured to deliver a pre-vapor formulation to a vaporizer.

Description of Related Art

Electronic vaping devices may include a heater and a wick extending into a reservoir that is configured to store a pre-vapor formulation.

SUMMARY

At least one example embodiment relates to reservoir assembly for an electronic vaping device.

In at least one example embodiment, a reservoir assembly for an electronic vaping device includes a reservoir configured to store a pre-vapor formulation, a tube including a first end and a second end, and a sleeve at least partially surrounding the second end of the tube. The first end of the tube extends into the reservoir. The second end of the tube protrudes from the reservoir. The tube includes a hole in a sidewall of the tube at the second end. The sleeve is formed of a wicking material. The sleeve is in fluid communication with the hole in the sidewall of the tube.

In at least one example embodiment, the sleeve is formed of a porous material. The porous material may include at least one of cellulose, fiberglass, and quartz.

In at least one example embodiment, the sleeve is heat resistant. The sleeve may include a plurality of fibers.

In at least one example embodiment, the tube has an inner diameter ranging from about 1.5 mm to about 3.0 mm. The hole in the sidewall of the tube may have a diameter ranging from about 0.5 mm to about 1 mm.

In at least one example embodiment, the sleeve friction fits around the second end of the tube.

At least one example embodiment relates to an electronic vaping device.

In at least one example embodiment, an electronic vaping device includes a housing extending in a longitudinal direction, a reservoir support inside the housing, a reservoir configured to store a pre-vapor formulation, a tube including a first end and a second end, a sleeve at least partially surrounding the second end of the tube, a heating element in fluid communication with the sleeve, and a power supply configured to supply power to the heating element.

In at least one example embodiment, the reservoir is held in place in the housing by the reservoir support. The first end of the tube extends into the reservoir, and the second end of the tube protrudes from the reservoir. The tube includes a hole in a sidewall of the tube at the second end of the tube. In at least one example embodiment, the sleeve is formed of a wicking material. The sleeve is in fluid communication with the hole in the sidewall of the tube.

In at least one example embodiment, the sleeve is formed of a porous material. The porous material may include at least one of cellulose, fiberglass, and quartz.

In at least one example embodiment, the sleeve is heat resistant. The sleeve may include a plurality of fibers.

In at least one example embodiment, the tube has an inner diameter ranging from about 1.5 mm to about 3.0 mm. The sleeve may friction fit around the second end of the tube.

In at least one example embodiment, the hole in the sidewall of the tube has a diameter ranging from about 0.5 mm to about 1 mm.

In at least one example embodiment, the electronic vaping device may also include at least one air inlet configured to allow air to flow into the housing, a sensor configured to sense airflow, and a control circuit in communication with the sensor and configured to initiate heating of the heating element.

In at least one example embodiment, the reservoir may further include a refill inlet configured to allow the reservoir to be filled with a pre-vapor formulation, and a refill inlet plug configured to seal the refill inlet.

In at least one example embodiment, the heating element is a planar heating element in contact with at least a portion of the sleeve.

In at least one example embodiment, the heating element is a coil heater that at least partially surrounds the sleeve.

BRIEF DESCRIPTION OF THE DRAWINGS

The various features and advantages of the non-limiting embodiments herein may become more apparent upon review of the detailed description in conjunction with the accompanying drawings. The accompanying drawings are merely provided for illustrative purposes and should not be interpreted to limit the scope of the claims. The accompanying drawings are not to be considered as drawn to scale unless explicitly noted. For purposes of clarity, various dimensions of the drawings may have been exaggerated.

DETAILED DESCRIPTION OF EXAMPLE EMBODIMENTS

Figure 1:
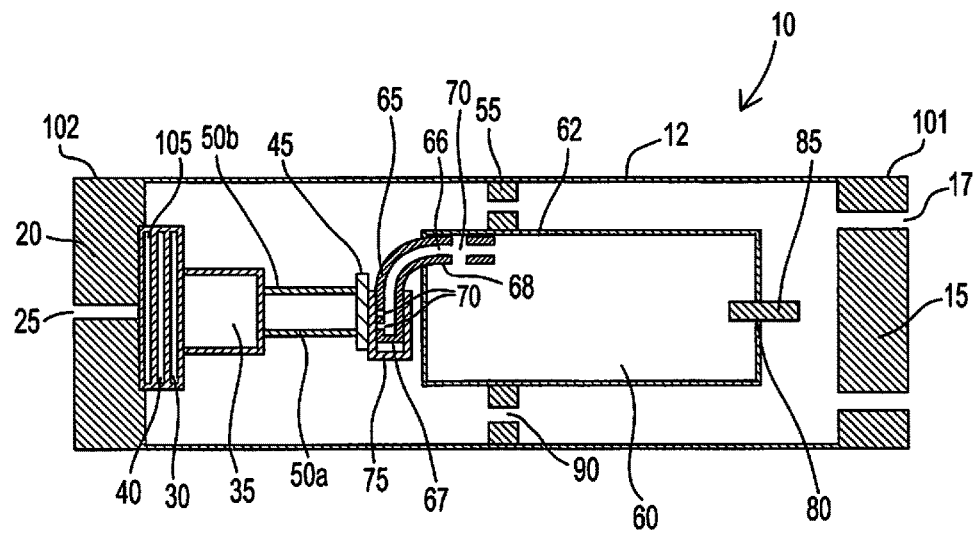
FIG. 1 is a side, cross-sectional view of an electronic vaping device according to at least one example embodiment.

Some detailed example embodiments are disclosed herein. However, specific structural and functional details disclosed herein are merely representative for purposes of describing example embodiments. Example embodiments may, however, be embodied in many alternate forms and should not be construed as limited to only the example embodiments set forth herein.

Accordingly, while example embodiments are capable of various modifications and alternative forms, example embodiments thereof are shown by way of example in the drawings and will herein be described in detail. It should be understood, however, that there is no intent to limit example embodiments to the particular forms disclosed, but to the contrary, example embodiments are to cover all modifications, equivalents, and alternatives falling within the scope of example embodiments. Like numbers refer to like elements throughout the description of the figures.

It should be understood that when an element or layer is referred to as being "on," "connected to," "coupled to," or "covering" another element or layer, it may be directly on, connected to, coupled to, or covering the other element or layer or intervening elements or layers may be present. In contrast, when an element is referred to as being "directly on," "directly connected to," or "directly coupled to" another element or layer, there are no intervening elements or layers present. Like numbers refer to like elements throughout the specification. As used herein, the term "and/or" includes any and all combinations of one or more of the associated listed items.

It should be understood that, although the terms first, second, third, etc. may be used herein to describe various elements, components, regions, layers and/or sections, these elements, components, regions, layers, and sections should not be limited by these terms. These terms are only used to distinguish one element, component, region, layer, or section from another region, layer, or section. Thus, a first element, component, region, layer, or section discussed below could be termed a second element, component, region, layer, or section without departing from the teachings of example embodiments.

Spatially relative terms (e.g., "beneath," "below," "lower," "above," "upper," and the like) may be used herein for ease of description to describe one element or feature's relationship to another element(s) or feature(s) as illustrated in the figures. It should be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the term "below" may encompass both an orientation of above and below. The device may be otherwise oriented (rotated 90 degrees or at other orientations) and the spatially relative descriptors used herein interpreted accordingly.

The terminology used herein is for the purpose of describing various example embodiments only and is not intended to be limiting of example embodiments. As used herein, the singular forms "a," "an," and "the" are intended to include the plural forms as well, unless the context clearly indicates otherwise. It will be further understood that the terms "includes," "including," "comprises," and/or "comprising," when used in this specification, specify the presence of stated features, integers, steps, operations, elements, and/or components, but do not preclude the presence or addition of one or more other features, integers, steps, operations, elements, components, and/or groups thereof.

Example embodiments are described herein with reference to cross-sectional illustrations that are schematic illustrations of idealized embodiments (and intermediate structures) of example embodiments. As such, variations from the shapes of the illustrations as a result, for example, of manufacturing techniques and/or tolerances, are to be expected. Thus, example embodiments should not be construed as limited to the shapes of regions illustrated herein but are to include deviations in shapes that result, for example, from manufacturing.

Unless otherwise defined, all terms (including technical and scientific terms) used herein have the same meaning as commonly understood by one of ordinary skill in the art to which example embodiments belong. It will be further understood that terms, including those defined in commonly used dictionaries, should be interpreted as having a meaning that is consistent with their meaning in the context of the relevant art and will not be interpreted in an idealized or overly formal sense unless expressly so defined herein.

FIG. 1 is a side, cross-sectional view of an electronic vaping device according to at least one example embodiment.

In at least one example embodiment, as shown in FIG. 1, an electronic vaping device 10 may include a housing 12 extending in a longitudinal direction. The housing 12 may contain a reservoir assembly 62, a heater 45, a power supply 35, a sensor 40 responsive to air drawn into the housing 12 via an air inlet 25, and a control circuit 30.

In at least one example embodiment, the reservoir assembly 62 includes a reservoir 60 that may be configured to store a pre-vapor formulation. The heater 45 may vaporize the pre-vapor formulation. In at least one example embodiment, the electronic vaping device 10 may include the features set forth in U.S. Patent Application Publication No. 2013/0192623 to Tucker et al. filed Jan. 31, 2013, the entire contents of which is incorporated herein by reference thereto.

In at least one example embodiment, the pre-vapor formulation is a material or combination of materials that may be transformed into a vapor. For example, the pre-vapor formulation may be a liquid, solid and/or gel formulation including, but not limited to, water, beads, solvents, active ingredients, ethanol, plant extracts, natural or artificial flavors, and/or vapor formers such as glycerin and propylene glycol. The pre-vapor formulation may include those described in U.S. Patent Application Publication No. 2015/0020823 to Lipowicz et al. filed Jul. 16, 2014 and U.S. Patent Application Publication No. 2015/0313275 to Anderson et al. filed Jan. 21, 2015, the entire content of each of which is incorporated herein by reference thereto.

In at least one example embodiment, the reservoir 60 may be sized and configured to hold enough pre-vapor formulation such that the electronic vaping device 10 may be configured for vaping for at least about 200 seconds. Moreover, the electronic vaping device 10 may be configured to allow each puff to last a maximum of about 5 seconds.

In at least one example embodiment, as shown in 1, the reservoir assembly 62 may include the reservoir 60, a tube 65, and a sleeve 75 circumscribing the tube 65. The reservoir assembly 62 may be removable from the housing 12. In at least one example embodiment, the reservoir assembly 62 may be replaced with another reservoir assembly 62 without removing and/or replacing the heater. In at least one example embodiment, a reservoir support 55 may be included on an inner surface of the housing 12. The reservoir support 55 may hold the reservoir assembly 62 in place within the electronic vaping device 10 via friction fit, snap fit, or any other suitable mechanism. The reservoir support 55 may be configured to prevent insertion of the reservoir assembly 62 past a desired location.

In at least one example embodiment, the reservoir 60 may be filled with the pre-vapor formulation via a fill hole 80. Once filled, the fill hole 80 may be sealed with a plug 85.

In at least one example embodiment, the reservoir assembly 62 may be disposable. Thus, the reservoir assembly 62 may be replaced once the pre-vapor formulation is depleted.

In at least one example embodiment, when the reservoir assembly 62 is inserted in the housing 12, the pre-vapor formulation may be transferred from the reservoir 60 to the proximity of the heater 45 via the tube 65 and the sleeve 75.

In at least one example embodiment, the tube 65 may include a first end 66 and a second end 67. In at least one example embodiment, the tube 65 includes a sidewall 68. At least one hole 70 extends through the sidewall 68 of the tube 65. The hole 70 may be at and/or adjacent the second end 67 of the tube. The first end 66 of the tube 65 may extend into the reservoir 60. In at least one example embodiment, at least one hole 70 may extend through the sidewall 68 at the first end 66 of the tube 65. The second end 67 of the tube 65 may be open, include an additional hole 70, and/or be sealed.

In at least one example embodiment, the at least one hole 70 may have a diameter ranging from about 0.5 mm to about 1.5 mm (e.g., about 0.75 mm to about 1.25 mm). The tube 65 may include 1 to 20 holes (e.g., about 2 to about 18, about 4 to about 16, or about 6 to about 14) through the sidewall 68 thereof. The holes 70 may be substantially the same size and/or may be substantially uniformly spaced along the second end 67 of the tube.

In at least one example embodiment, the tube 65 may include a plurality of holes 70 extending through the sidewall 68. The holes 70 may have different diameters. In at least one example embodiment, the diameters of the holes 70 may increase or decrease along a length of the tube 65. For example, larger holes may be formed at the second end 67 of the tube 65, and smaller holes 70 may be formed closer to the first end 66 of the tube 65. In at least one example embodiment, the holes 70 are non-uniformly spaced along the tube 65.

In at least one example embodiment, the sleeve 75 may friction fit about a portion of the tube 65 and may help minimize and/or avoid leakage of the pre-vapor formulation from the holes 70 in the tube 75. The pre-vapor formulation may travel through the tube 65 by capillary action and/or gravity. The pre-vapor formulation exits the tube 65 through the at least one hole 70. The sleeve 75 catches the pre-vapor formulation as the pre-vapor formulation exits the at least one hole 70 and wicks the pre-vapor formulation along the sleeve 75 and towards the heater 45.

In at least one example embodiment, the tube 65 may be formed of plastic, glass, and metal. The tube 65 may have an inner diameter ranging from about 1 mm to about 5 mm (e.g., about 1.5 mm to about 4.5 mm, about 2.0 mm to about 4.0 mm, or about 2.5 mm to about 3.5 mm). The tube 65 may have a length ranging from about 5 mm to about 50 mm (e.g., about 10 mm to about 45 mm, about 15 mm to about 40 mm, about 20 mm to about 35 mm, or about 25 mm to about 30 mm). The tube 65 may include one or more bends.

In at least one example embodiment, the sleeve 75 may be about 0.5 mm to about 2.0 mm thick (e.g., about 1.0 mm to about 1.5 mm thick) and about 0.5 mm to about 20 mm in length (e.g., about 1 mm to about 15 mm or about 5 mm to about 10 mm).

In at least one example embodiment, the sleeve 75 may be formed of any suitable wicking material that is heat resistant. For example, the sleeve 75 may be formed of a porous material such as cellulose, ceramic, glass, and/or quartz. In at least one example embodiment, the sleeve 75 may be formed of a woven or non-woven material, and the pre-vapor formulation may move along and/or through the sleeve 75 via capillary action. In at least one example embodiment, the sleeve 75 may include a plurality of filaments that may be generally aligned. The filaments may have a cross-section that is generally cross-shaped, clover-shaped, Y-shaped, or in any other suitable shape.

In at least one example embodiment, the sleeve 75 may have any suitable capillarity drawing action to accommodate pre-vapor formulations having different physical properties such as density, viscosity, surface tension and vapor pressure.

In at least one example embodiment, the housing 12 may have a generally cylindrical cross-section. In other example embodiments, the housing 12 may have a generally triangular cross-section. In some example embodiments, the housing 12 may have a greater circumference or dimensions at a second end (tip end) than at a first end (mouth-end) of the electronic vaping device 10.

In at least one example embodiment, the air inlet 25 may be machined into the housing 12 with precision tooling such that a diameter is closely controlled and replicated from one electronic vaping device 10 to the next during manufacture.

In at least one example embodiment, the air inlet may be formed through an end cap 20, as shown in FIG. 1.

In at least one example embodiment, the air inlet 25 may be sized and configured such that the electronic vaping device 10 has a resistance-to-draw (RTD) in the range of from about 60 mm $H_2O$ to about 150 mm $H_2O$.

In at least one example embodiment, the heater 45 is electrically connected to the power supply 35 via one or more electrical leads 50a, 50b. The heater 45 may include a planar heater including platinum coated on ceramic. In at least one example embodiment, the heater 45 is a wire coil heater.

In at least one example embodiment, the heater 45 may be formed of any suitable electrically resistive materials. Examples of suitable electrically resistive materials may include, but not limited to, titanium, zirconium, tantalum and metals from the platinum group. Examples of suitable metal alloys include, but not limited to, stainless steel, nickel, cobalt, chromium, aluminum-titanium-zirconium, hafnium, niobium, molybdenum, tantalum, tungsten, tin, gallium, manganese and iron-containing alloys, and super-alloys based on nickel, iron, cobalt, stainless steel. For example, the heater 45 may be formed of nickel aluminide, a material with a layer of alumina on the surface, iron aluminide and other composite materials, the electrically resistive material may optionally be embedded in, encapsulated or coated with an insulating material or vice-versa, depending on the kinetics of energy transfer and the external physicochemical properties required. The heater 45 may include at least one material selected from the group consisting of stainless steel, copper, copper alloys, nickel-chromium alloys, super alloys and combinations thereof. In an example embodiment, the heater 45 may be formed of nickel-chromium alloys or iron-chromium alloys. In another example embodiment, the heater 45 may be a ceramic heater having an electrically resistive layer on an outside surface thereof.

In at least one example embodiment, the heater 45 may heat pre-vapor formulation in the sleeve 75 by thermal conduction. Alternatively, heat from the heater 45 may be conducted to the pre-vapor formulation by means of a heat conductive element or the heater 45 may transfer heat to the incoming ambient air that is drawn through the electronic vaping device 10 during vaping, which in turn heats the pre-vapor formulation by convection.

In at least one example embodiment, the heater 45 may be a porous material which incorporates a resistance heater formed of a material having a high electrical resistance capable of generating heat quickly.

In at least one example embodiment, the power supply 35 may include a battery arranged in the electronic vaping device 10. The power supply 35 may be a Lithium-ion battery or one of its variants, for example a Lithium-ion polymer battery. Alternatively, the power supply 35 may be a nickel-metal hydride battery, a nickel cadmium battery, a lithium-manganese battery, a lithium-cobalt battery or a fuel cell. The electronic vaping device 10 may be usable by an adult vaper until the energy in the power supply 35 is depleted or in the case of lithium polymer battery, a minimum voltage cut-off level is achieved.

In at least one example embodiment, the power supply 35 may be rechargeable and may include circuitry configured to allow the power supply 35 to be chargeable by an external charging device. To recharge the electronic vaping device 10, an USB charger or other suitable charger assembly may be used.

Furthermore, the electronic vaping device 10 may include the control circuit 30 and the sensor 40 (e.g., a microelectromechanical sensor (MEMS)). The sensor 40 may be configured to sense an air pressure drop and initiate application of voltage from the power supply 35 to the heater 45. The control circuit 30 may also include a heater activation light 105 configured to glow when the heater 45 is activated. The heater activation light 105 may include a light-emitting diode (LED) and may be at the second end 102 of the electronic vaping device 10. Moreover, the heater activation light 105 may be arranged to be visible to an adult vapor during vaping. In addition, the heater activation light 105 may be utilized for e-vaping system diagnostics or to indicate that recharging is in progress. The heater activation light 105 may also be configured such that the adult vapor may activate and/or deactivate the heater activation light 105 for privacy.

In at least one example embodiment, when activated, the heater 45 may heat a portion of the sleeve 75 for less than about 10 seconds. Thus, the power cycle may range in period from about 2 seconds to about 10 seconds (e.g., about 3 seconds to about 9 seconds, about 4 seconds to about 8 seconds or about 5 seconds to about 7 seconds).

As shown in FIG. 1, in at least one example embodiment, a mouth-end insert 15 can be positioned at the first end 101 of the electronic vaping device 10. The mouth-end insert 15 may include at least two outlets 17, which may be located off-axis from the longitudinal axis of the electronic vaping device 10. The outlets 17 may be angled outwardly in relation to the longitudinal axis of the electronic vaping device 10. The outlets 17 may be substantially uniformly distributed about the perimeter of the mouth-end insert 15 so as to substantially uniformly distribute vapor.

Figure 2:
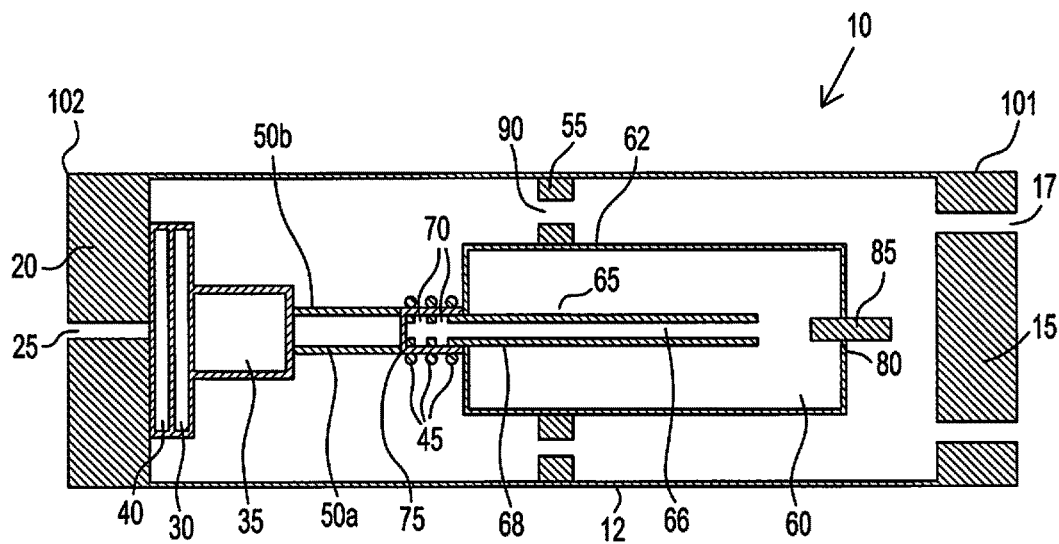
FIG. 2 is a side, cross-sectional view of an electronic vaping device according to at least one example embodiment.

FIG. 2 is a side, cross-sectional view of an electronic vaping device according to at least one example embodiment.

In at least one example embodiment, as shown in FIG. 2, the electronic vaping device 10 is the same as the electronic vaping device of FIG. 1, except that the tube 65 is straight and the heater 45 at least partially surrounds a portion of the sleeve 75.

In at least one example embodiment, the heater 45 may be a wire coil heater that at least partially surrounds a portion of the sleeve 75. In some example embodiments, the heater coil 45 may or may not be in contact with the sleeve 75.

In at least one example embodiment, the electronic vaping device 10 may be about 80 mm to about 110 mm long and about 7 mm to about 8 mm in diameter. For example, in one example embodiment, the electronic vaping device 10 may be about 84 mm long and may have a diameter of about 7.8 mm.

In at least one example embodiment, the reservoir assembly may include a tube that is generally U-shaped with two ends extending into the reservoir (not shown). Holes may extend through a central portion of the tube, and a sleeve may circumscribe the tube at the location of the holes.

While a number of example embodiments have been disclosed herein, it should be understood that other variations may be possible. Such variations are not to be regarded as a departure from the spirit and scope of the present disclosure, and all such modifications as would be obvious to one skilled in the art are intended to be included within the scope of the following claims.

I claim:

1. A reservoir assembly for an electronic vaping device, the reservoir assembly comprising:
   a reservoir configured to store a pre-vapor formulation;
   a non-porous tube including a first end and a second end, the first end extending into the reservoir, the second end protruding from the reservoir, and the non-porous tube including at least one hole in a sidewall of the non-porous tube at the second end; and
   a sleeve at least partially surrounding the second end of the non-porous tube, the sleeve formed of a wicking material, the sleeve in fluid communication with the at least one hole in the sidewall of the non-porous tube.

2. The reservoir assembly of claim 1, wherein the sleeve wicking material includes a porous material.

3. The reservoir assembly of claim 2, wherein the porous material includes cellulose, fiberglass, quartz, a sub-combination thereof, or a combination thereof.

4. The reservoir assembly of claim 1, wherein the sleeve is heat resistant.

5. The reservoir assembly of claim 1, wherein the sleeve includes a plurality of fibers.

6. The reservoir assembly of claim 1, wherein the non-porous tube has an inner diameter ranging from about 1.5 mm to about 3.0 mm.

7. The reservoir assembly of claim 1, wherein the sleeve friction fits around the second end of the non-porous tube.

8. The reservoir assembly of claim 1, wherein the at least one hole has a diameter ranging from about 0.5 mm to about 1 mm.

9. An electronic vaping device comprising:
   a housing extending in a longitudinal direction;
   a reservoir support inside the housing;
   a reservoir configured to store a pre-vapor formulation, the reservoir held in place in the housing by the reservoir support;
   a non-porous tube including a first end and a second end, the first end extending into the reservoir, the second end protruding from the reservoir, and the non-porous tube including at least one hole in a sidewall of the non-porous tube at the second end;
   a sleeve at least partially surrounding the second end of the non-porous tube, the sleeve formed of a wicking material, and the sleeve in fluid communication with the at least one hole in the sidewall of the non-porous tube;
   a heating element in fluid communication with the sleeve; and
   a power supply configured to supply-power to the heating element.

10. The electronic vaping device of claim 9, wherein the wicking material includes a porous material.

11. The electronic vaping device of claim 10, wherein the porous material includes cellulose, fiberglass, quartz, a sub-combination thereof, or a combination thereof.

12. The electronic vaping device of claim 9, wherein the sleeve is heat resistant.

13. The electronic vaping device of claim 9, wherein the sleeve includes a plurality of fibers.

14. The electronic vaping device of claim 9, wherein the at least one tube has an inner diameter ranging from about 1.5 mm to about 3.0 mm.

15. The electronic vaping device of claim 9, wherein the sleeve friction fits around the second end of the non-porous tube.

16. The electronic vaping device of claim 9, wherein the at least one hole has a diameter ranging from about 0.5 mm to about 1 mm.

17. The electronic vaping device of claim 9, further comprising:

at least one air inlet configured to allow air to flow into the housing;

a sensor configured to sense airflow; and a control circuit in communication with the sensor.

18. The electronic vaping device of claim 9, wherein the reservoir further comprises:

a refill inlet configured to allow the reservoir to be filled with a pre-vapor formulation; and a refill inlet plug configured to seal the refill inlet.

19. The electronic vaping device of claim 9, wherein the heating element is a planar heating element in contact with at least a portion of the sleeve.

20. The electronic vaping device of claim 9, wherein the heating element is a coil heater that at least partially surrounds the sleeve.

* * * * *